United States Patent
Katra

(10) Patent No.: US 12,109,020 B2
(45) Date of Patent: Oct. 8, 2024

(54) SYSTEM AND METHOD FOR NON-INVASIVE MONITORING OF ADVANCED GLYCATION END-PRODUCTS (AGE)

(71) Applicant: Medtronic Monitoring, Inc., San Jose, CA (US)

(72) Inventor: Rodolphe Katra, Blaine, MN (US)

(73) Assignee: Medtronic Monitoring, Inc., San Jose, CA (US)

( * ) Notice: Subject to any disclaimer, the term of this patent is extended or adjusted under 35 U.S.C. 154(b) by 494 days.

(21) Appl. No.: 17/365,719

(22) Filed: Jul. 1, 2021

(65) Prior Publication Data

US 2021/0321912 A1    Oct. 21, 2021

Related U.S. Application Data

(62) Division of application No. 15/866,160, filed on Jan. 9, 2018, now Pat. No. 11,051,727.

(51) Int. Cl.
 *A61B 5/1455* (2006.01)
 *A61B 5/00* (2006.01)
 *A61B 5/145* (2006.01)
 *G01N 27/327* (2006.01)

(52) U.S. Cl.
 CPC .......... *A61B 5/1455* (2013.01); *A61B 5/0071* (2013.01); *A61B 5/14532* (2013.01); *G01N 27/3271* (2013.01)

(58) Field of Classification Search
 CPC .............. A61B 5/1455; A61B 5/14551; A61B 5/14552; A61B 5/14532; A61B 5/0071; A61B 5/14546; A61B 5/14556; A61B 5/1459
 See application file for complete search history.

(56) References Cited

U.S. PATENT DOCUMENTS

| | | |
|---|---|---|
| 5,372,136 A | 12/1994 | Steuer et al. |
| 5,377,674 A | 1/1995 | Kuestner |
| 5,377,675 A | 1/1995 | Ruskewicz et al. |
| 5,551,422 A | 9/1996 | Simonsen et al. |
| 5,692,503 A | 12/1997 | Kuenstner |
| 5,692,504 A | 12/1997 | Essenpreis et al. |

(Continued)

FOREIGN PATENT DOCUMENTS

| | | | |
|---|---|---|---|
| WO | 9313706 A2 | 7/1993 | |
| WO | WO-0122869 A1 * | 4/2001 | ........... A61B 5/0059 |

(Continued)

OTHER PUBLICATIONS

Examination Report from counterpart European Application No. 19706736.6 dated Nov. 24, 2021, 6 pp.

(Continued)

*Primary Examiner* — Chu Chuan Liu
(74) *Attorney, Agent, or Firm* — Shumaker & Sieffert, P.A.

(57) ABSTRACT

A method of non-invasively monitoring advanced glycation end-product (AGE) concentrations includes providing incident light to patient tissue at one or more excitation wavelengths and monitoring the one or more emission responses at one or more emission wavelengths. Based on the emission responses monitored, a ratio is calculated based on a ratio of the first emission response to the second emission response.

18 Claims, 12 Drawing Sheets

(56) References Cited

U.S. PATENT DOCUMENTS

| | | | |
|---|---|---|---|
| 6,064,474 | A | 5/2000 | Lee et al. |
| 6,526,298 | B1 | 2/2003 | Khalil et al. |
| 6,606,509 | B2 | 8/2003 | Schmitt |
| 6,728,560 | B2 | 4/2004 | Kollias et al. |
| 7,139,598 | B2 | 11/2006 | Hull et al. |
| 8,078,243 | B2 | 12/2011 | Ediger et al. |
| 8,121,671 | B2 | 2/2012 | Hull et al. |
| 8,131,332 | B2 | 3/2012 | Maynard et al. |
| 8,172,459 | B2 | 5/2012 | Abreu |
| 8,238,993 | B2 | 8/2012 | Maynard et al. |
| 8,320,981 | B1 | 11/2012 | Mayer et al. |
| 8,346,332 | B2 | 1/2013 | Kuhn et al. |
| 8,480,581 | B2 | 7/2013 | Zhang et al. |
| 8,571,620 | B2 | 10/2013 | Cinbis et al. |
| 8,676,283 | B2 | 3/2014 | Matter et al. |
| 11,039,768 | B2 | 6/2021 | Katra |
| 11,051,727 | B2 | 7/2021 | Katra |
| 2002/0038079 | A1 | 3/2002 | Steuer et al. |
| 2002/0082489 | A1 | 6/2002 | Casciani et al. |
| 2002/0165439 | A1 | 11/2002 | Schmitt |
| 2003/0018241 | A1 | 1/2003 | Mannheimer |
| 2004/0225207 | A1 | 11/2004 | Bae et al. |
| 2006/0195022 | A1* | 8/2006 | Trepagnier ........... A61B 5/1455 600/316 |
| 2007/0156036 | A1 | 7/2007 | Pilon et al. |
| 2008/0214911 | A1 | 9/2008 | Forstner |
| 2009/0118666 | A1 | 5/2009 | Blomqvist et al. |
| 2010/0099964 | A1 | 4/2010 | O'Reilly et al. |
| 2010/0110416 | A1 | 5/2010 | Barrett et al. |
| 2010/0185252 | A1 | 7/2010 | Björling et al. |
| 2010/0249865 | A1 | 9/2010 | Zhang et al. |
| 2010/0268090 | A1 | 10/2010 | Rubinstein et al. |
| 2010/0280499 | A1 | 11/2010 | Yodfat et al. |
| 2010/0298675 | A1 | 11/2010 | Al-Ali et al. |
| 2012/0277546 | A1 | 11/2012 | Soykan et al. |
| 2013/0178724 | A1* | 7/2013 | Ting ................... A61B 5/14532 600/479 |
| 2013/0217984 | A1 | 8/2013 | Graaff et al. |
| 2015/0073243 | A1 | 3/2015 | Taub et al. |
| 2015/0201839 | A1 | 7/2015 | Kang et al. |
| 2015/0245799 | A1 | 9/2015 | Gretz et al. |
| 2016/0061810 | A1 | 3/2016 | Kim et al. |
| 2016/0367188 | A1* | 12/2016 | Malik ................... A61B 5/0205 |
| 2016/0371452 | A1 | 12/2016 | Landrum et al. |
| 2019/0209055 | A1 | 7/2019 | Katra |
| 2019/0209060 | A1 | 7/2019 | Katra |
| 2019/0209061 | A1 | 7/2019 | Katra |

FOREIGN PATENT DOCUMENTS

| | | |
|---|---|---|
| WO | 2003077761 A1 | 9/2003 |
| WO | 2011159148 A2 | 12/2011 |
| WO | 2012005696 A1 | 1/2012 |

OTHER PUBLICATIONS

Office Action from U.S. Appl. No. 17/352,649 dated Jun. 30, 2023, 13 pp.
Notice of Allowance from U.S. Appl. No. 17/352,649 dated Oct. 30, 2023, 5 pp.
Response to Office Action dated Jun. 30, 2023 from U.S. Appl. No. 17/352,649, filed Oct. 2, 2023, 12 pp.
Anand et al., "Anemia and Change in Hemoglobin Over Time Related to Mortality and Morbidity in Patients With Chronic Heart Failure", Circulation, Aug. 15, 2005, vol. 112, No. 8, pp. 1121-1127.
Blackwell et al., "In Vivo Time-Resolved Autofluorescense Measurements to Test for Glycation of Human Skin", Journal of Biomedical Optics, vol. 13 No. 1, Jan./Feb. 2008, 15 pp.
Carneiro, "Haemoglobin and Haematocrit: is the Threefold Conversion Valid for Assessing Anaemia in Malariaendemic Settings," Malaria Journal, vol. 6, No. 67, May 22, 2007, 5 pp.
Ciobanu, et al., "Fiuorophores Advanced Glycation End Products (AGEs)-to-NADH Ratio is Predictor for Diabetic Chronic Kidney and Cardiovascular Disease", Journal Diabetes Complications, vol. 29, No. 7, Sep.-Oct. 2015, pp. 893-897.
De Den US, et al., "Temporal Variations in Hematocrit Values in Patients with Left Ventricular Dysfunction: Relationship with Cause-Specific Mortality and Morbidity and Optimal Monitoring—Further Insights from SOLVD", Canadian Journal of Cardiology, vol. 24, No. 1, Jan. 2008, pp. 45-48.
Ediger, et al., "Noninvasive Optical Detection of Impaired Glucose Tolerance: A Comparison Against FPG and A1C", 62, Review of Endocrinology, Jun. 2007.
Hartog, et al., "Advanced glycation end-products (AGEs) and hearth failure: Pathophysiology and clinical implications", European Journal of Heart Failure, vol. 9, No. 12, Dec. 2007, pp. 1146-1155.
Heike, et al., "Measurement of Transcutaneous Hemoglobin Concentration by Noninvasive White-Light", Pediatrics, vol. 116, No. 4, Oct. 2005, pp. 841-843.
Horecker, "The Absorption Spectra of Hemoglobin and its Deriavitives in the Visible and Near Infra-Red Regions", Journal of Biological Chemistry, Dec. 3, 1942, pp. 173-183.
International Search Report and Written Opinion of International Application No. PCT/IB2019/050235, mailed Apr. 26, 2019, 13 pp.
Jeon, et al., "Noninvasive Total Hemoglobin Measurement", Journal of Biomedical Optics, vol. 7, No. 1, Jan. 2020, 45-50.
Li et al., "Advanced Glycation End Products Bisphasically Modulate Bone Resorption in Osteoclast-like Cells", American Journal of Physiology, Endocrinology and Metabolism, vol. 310, No. 5, Dec. 15, 2016, E355-E366.
Lowndes, "Blood Interference in Fluorescence Spectrum—Experiment, Analysis and Comparison with Intra-operative Measurements on Brain Tumor", Linkoping University, Jul. 9, 2010, 42 pages.
McMurdy, et al., "Noninvasive Optical, Electrical, and Acoustic Methods of Total Hemoglobin Determination", Clinical Chemistry, vol. 54, No. 2, Feb. 2008, pp. 264-272.
Notification of Transmittal of the International Search Report and the Written Opinion of the International Searching Authority, or the Declaration for PCT/182019/050235.
Notification of Transmittal of the International Search Report and the Written Opinion of the International Searching Authority, or the Declaration for PCT/182019/050236 mailed Apr. 26, 2019.
Notification of Transmittal of the International Search Report and the Written Opinion of the International Searching Authority, or the Declaration for PCT/182019/050238 mailed Jun. 26, 2019.
Pandey, et al., "Emerging Trends in Optical Sensing of Glycemic Markers for Diabetes Monitoring", Trends in Analytical Chemistry, vol. 64, Jan. 1, 2015, pp. 100-108.
Rabe, et al., "Measurement of Transcutaneous Hemoglobin Concentration by Noninvasive White-Light Spectroscopy in Infants", Pediatrics, vol. 116, No. 4, Oct. 2005, pp. 841-843.
Response to Communication Pursuant to Rules 161(1) and 162 from European Patent Application No. 19706736.6, dated Aug. 18, 2020, filed Feb. 2, 2021, 17 pp.
Wong, et al., "Augmentation of the Neutrophil Respitory Burst Through the Action of Advanced Glycation End Products", Diabetes, vol. 51 No. 9, Sep. 2002, pp. 2846-2853.
U.S. Appl. No. 17/352,649, filed Jun. 21, 2021, by Katra.
Prosecution History from U.S. Appl. No. 15/866,160, dated Jun. 29, 2020 through May 12, 2021, 34 pp.
Prosecution History from U.S. Appl. No. 15/866,036, dated Jul. 2, 2020 through May 12, 2021, 55 pp.
Prosecution History from U.S. Appl. No. 15/866,118, dated Jul. 30, 2020 through Jun. 18, 2021, 64 pp.
Office Action from U.S. Appl. No. 17/452,190 dated Dec. 19, 2023, 17 pp.
Corrected Notice of Allowability from U.S. Appl. No. 17/352,649 dated Jan. 31, 2024, 2 pp.
Final Office Action from U.S. Appl. No. 17/452,190 dated Apr. 26, 2024, 18 pp.
Response to Office Action dated Dec. 19, 2023 from U.S. Appl. No. 17/452,190, filed Mar. 19, 2024, 13 pp.
Advisory Action from U.S. Appl. No. 17/452,190 dated Jun. 13, 2024, 3 pp.

(56) References Cited

OTHER PUBLICATIONS

Office Action from U.S. Appl. No. 17/452,190 dated Jul. 15, 2024, 18 pp.
Response to Final Office Action dated Apr. 26, 2024 from U.S. Appl. No. 17/452,190 filed Jun. 3, 2024, 16 pp.

* cited by examiner

SYSTEM AND METHOD FOR NON-INVASIVE MONITORING OF ADVANCED GLYCATION END-PRODUCTS (AGE)

This application is a divisional of U.S. patent application Ser. No. 15/866,160, filed Jan. 9, 2018, which issued as U.S. Pat. No. 11,051,727 on Jul. 6, 2021. The entire content of U.S. patent application Ser. No. 15/866,160 is incorporated herein by reference.

TECHNICAL FIELD

This invention relates generally to patient diagnosis and monitoring, and in particular non-invasive diagnosis and monitoring of advanced glycation end-products (AGE).

BACKGROUND

Advanced glycation end products (AGEs) are proteins or lipids that become glycated as a result of exposure to sugars. AGE is a factor in aging and in the development or worsening of many degenerative diseases, such as diabetes, atherosclerosis, chronic kidney disease, and Alzheimer's disease. AGE formation results from non-enzymatic reactions between sugars and proteins called the Maillard reaction. In the first step of this reaction, a sugar adduct (e.g., glucose) reacts with a protein amino group (e.g., $NH_2$). The Schiff-base then converts into a more stable Amadori product (e.g., glycated hemoglobin or HbA1c). This reaction may occur in vivo throughout the body, including the skin, neural, vascular, renal, cardiac tissue, as well as in the patient's blood (e.g., HbA1c). In patients with diabetes, accelerated AGE accumulation occurs mainly as a consequence of high glucose levels. Renal failure also contributes to enhanced AGE accumulation.

With respect to hemoglobin (Hb), when the body processes sugar, glucose in the bloodstream naturally attaches to hemoglobin, wherein the amount of glucose that combines with hemoglobin is directly proportional to the total amount of sugar in the patient at a given time. The amount of glycated hemoglobin (referred to herein as "HbA1c") is therefore a reflection of the amount of blood glucoses in a patient over the last several weeks. Monitoring of HbA1c is particularly important for patients with diabetes or pre-diabetes, and is an indicator as to whether the patient's diabetes is under control.

Similarly, AGE accumulation within the patient's heart can result in excessive cross-linking of myocardial tissue, which increases the rigidity of the tissue and may induce diastolic dysfunction in the heart. In addition, AGE accumulation has been linked to delays in calcium uptake resulting in longer re-polarisation times associated with the heart, and to the progression of coronary artery disease by negatively influencing LDL-metabolism.

Typically, monitoring AGE accumulation in patient tissue and/or blood requires taking a tissue sample from the patient or blood sample, and then analyzing the sample in a laboratory. This requires a patient to physically visit a healthcare center to provide the tissue/blood sample.

It would therefore be advantageous to develop a device that is capable of non-invasive monitoring of AGE accumulations, both in tissue and in blood.

SUMMARY

According to one embodiment, a method of non-invasively monitoring advanced glycation end-products (AGEs) concentration, the method includes providing incident light to patient tissue at a first excitation wavelength and monitoring a first emission response to the light provided at the first excitation wavelength. The method further includes providing incident light to patient tissue at a second excitation wavelength and monitoring a second emission response to the light provided at the second excitation wavelength. The AGE concentration is calculated based on a ratio of the first emission response to the second emission response.

According to another embodiment, a system for non-invasively monitoring of advanced glycation end-product (AGE) includes a medical device and a processing module. The medical device includes a first light emitter configured to provide a first excitation signal to patient tissue at a first wavelength, a second light emitter configured to provide a second excitation signal to patient tissue at a second wavelength, and at least one photodetector configured to monitor an emission response at a first emission wavelength, wherein the first emission wavelength is selected to correspond with a maximum of the emission response to either the first excitation signal or the second excitation signal. The processing module is configured to receive emission responses measured at the first emission wavelength in response to the first and the second excitation wavelengths, wherein the processing module calculates a ratio based on the received emission responses and utilizes the calculated ratio to determine the AGE concentration level.

A method of non-invasively monitoring advanced glycation end-products (AGEs) concentration, the method includes providing incident light to patient tissue at a first excitation wavelength. The first emission response is measured at a first emission wavelength and at a second emission wavelength. The AGE concentration is calculated based on a ratio of the first emission response to the second emission response.

DETAILED DESCRIPTION

Figure 1:
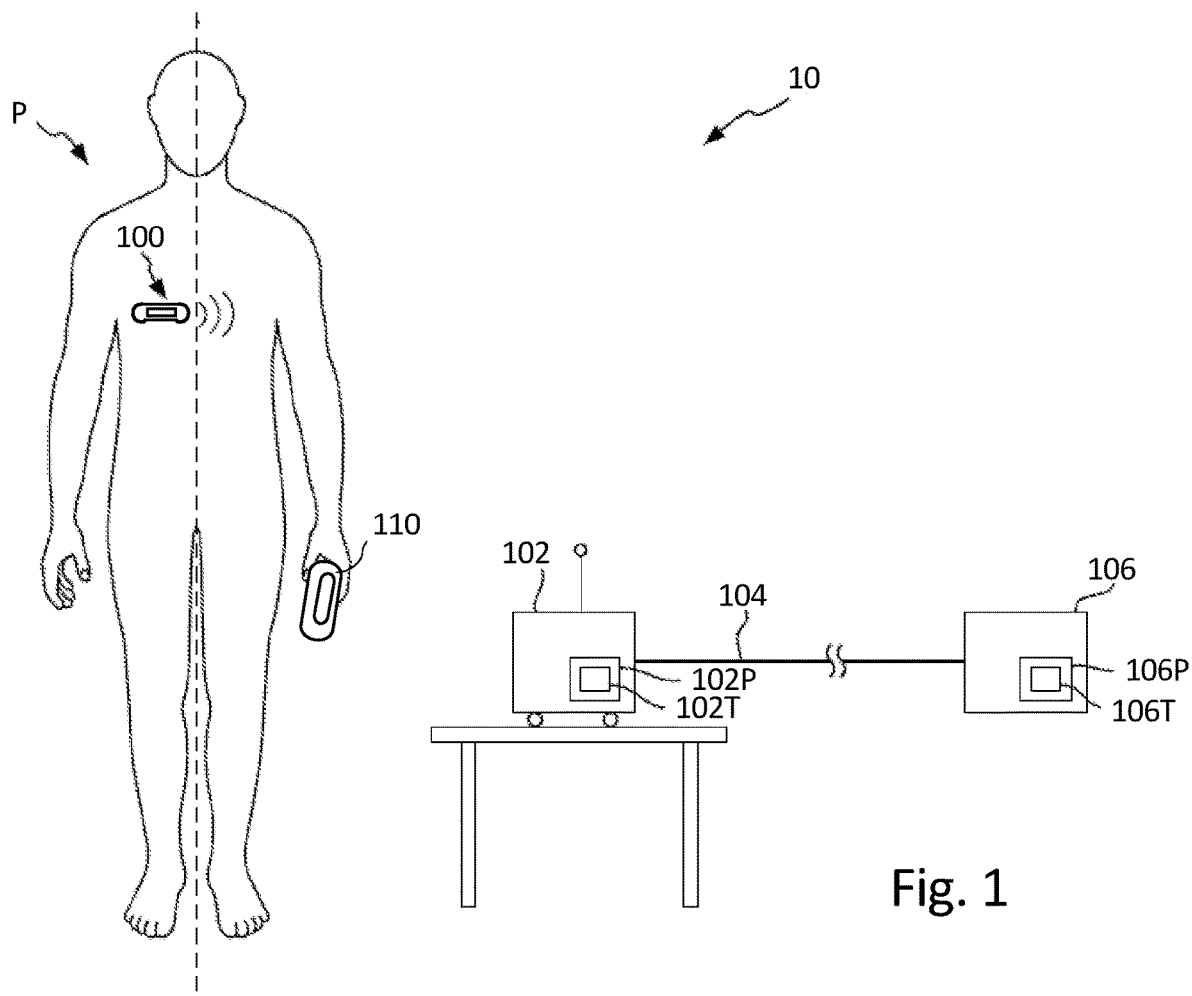
FIG. 1 illustrates a schematic view of a patient and a patient monitoring system, according to some embodiments.

Advanced glycation end products (AGEs) refer generally to proteins or lipids that become glycated as a result of exposure to sugars. The present invention can be utilized to non-invasively monitor various types of AGEs occurring in patient tissue. Depending on the particular AGE protein or lipid to be monitored, one or more excitation wavelengths are selected and one or more emission wavelengths are monitored. For example, patient tissue/blood may be exposed to two or more excitation wavelengths selected to generate a significant emission response (e.g., maximum and/or minimum associated with the particular AGE to be monitored), with first and second emission responses measured at one or more wavelengths. The ratio of the first and second emission responses are utilized to calculate the concentration of the particular AGE protein or lipid to be monitored. In another embodiment, patient tissue/blood may be exposed to a single excitation wavelength, with the emission response measured at first and second wavelengths, wherein the first and second wavelengths are selected to correspond with a significant emission response (e.g., autofluorescence, absorption, and reflectance maximums and/or minimums). The ratio of the emission response at first and second wavelengths is utilized once again to calculate the concentration of the particular AGE protein or lipid to be monitored. In another embodiment, patient tissue/blood may be exposed to at least one excitation wavelength selected to generate an emission response. The emission response is measured at one or more wavelengths over a period of time to generate first and second temporal emission responses. A ratio of the first and second temporal emission responses is utilized to calculate the concentration of the particular AGE protein or lipid to be monitored.

In particular, an example AGE species is glycated hemoglobin (HbA1c), which is utilized as an indicator for monitoring diabetes risk in patients. Typically, HbA1c testing requires drawing blood from the patient and providing the blood to a lab for analysis. The present disclosure provides a system and method for non-invasive monitoring of HbA1c utilizing optical measurements. In one embodiment, a first light source emits light at a first excitation wavelength and monitors the emission response. A second light source emits light at a second excitation wavelength and the emission response is again measured. The first and second excitation wavelengths are selected to provide emission responses related to hemoglobin and HbA1c, respectively. Based on a ratio of the amplitudes measured in response to the first and second excitation wavelengths, the concentration of HbA1c relative to hemoglobin concentration is determined.

Benefits of this system include the non-invasive nature of monitoring, and real-time feedback provided by using optical means of sensing AGE concentration levels. Although these levels change very slowly over time (e.g., 30-60 days), and thus do not require continuous monitoring, trends can be developed by monitoring AGE levels at a shorter duration than once every 30-60 days. In one embodiment, a daily measurement of AGE concentration levels can detect increasing levels of an AGE protein or lipid before it reaches problematic levels. For example, the risk of diabetes increases with increasing HbA1c levels, resulting in HbA1c concentrations being particularly useful for detecting pre-diabetes in patients. In addition, because the test can be done non-invasively and remote from a medical center/office, there is a greater probability of patient compliance.

FIG. 1 illustrates a patient P and a monitoring system 10 for non-invasive monitoring of AGE concentration levels (e.g., glycated hemoglobin (HbA1c)). In the embodiment shown in FIG. 1, monitoring system 10 comprises a patient medical device 100 and/or 110, gateway 102, and remote monitoring center 106. In the embodiment shown in FIG. 1, patient medical device 100 is an adherent device that attaches to the skin of the patient, and patient medical device 110 is a clip that fits over a patient's finger. In other embodiments, patient medical device may include implantable devices, insertable devices, injectable devices, arm cuff (similar to a blood pressure cuff) and/or wearable devices such as a Holter monitor (collectively referred to as a medical device). In each example, the patient medical device utilizes optical components to monitor AGE concentration levels (e.g., HbA1c levels) of the patient. In some embodiments, patient medical device 100 and/or 110 includes one or more additional sensors for monitoring one or more additional physiological parameters of the patient, such as activity, orientation, cardiac activity, hydration, etc.

The location of the patient medical device 100/110 may be selected based on the AGE protein and/or lipid to be monitored. For example, if AGE concentration levels in myocardial tissue are to be monitored, then the patient medical device may be adhered to the patient's thorax. The medical device may be affixed to the skin of the patient, subcutaneously, or implanted adjacent to the tissue to be excited.

In the embodiment shown in FIG. 1, medical device 100 is adhered to the thorax of patient P, which allows for the monitoring of additional physiological parameters, such as ECG, hydration, activity, etc. In many embodiments, the device may adhere to one side of the patient, from which side data can be collected. A benefit of utilizing an adherent device, implantable, injectable, and/or wearable device is that it may be utilized to collect physiological data from the patient while the patient goes about normal day-to-day activities outside of a hospital setting. A medical device clipped to a patient's finger, such as medical device 110, is not worn throughout the day by a patient, but may be useful in applications such as these due to the relative ease in applying the clip to a patient's finger in order to take a reading. That is, rather than wearing the device for an extended period of time, a patient may periodically clip the device to the patient's finger for a few moments (e.g., seconds) in order to non-invasively measure an AGE concentration level, and then removed. For applications such as AGEs monitoring, in which a single measurement a day may be sufficient, a medical device clipped to the patient's finger (or similarly, an arm cuff) may be sufficient.

As discussed above, in some embodiments, the medical device may monitor a number of physiological parameters associated with patient P, including optical signals utilized to determine AGE concentration levels, electrocardiogram (ECG) signals utilized to detect rhythm abnormalities such as tachycardia and/or bradycardia as well as activity level data, posture, bio-impedance, blood pressure (associated with a blood pressure cuff), etc. Analysis of one or more of these physiological parameters may be done locally by the medical devices 100 or 110, or remotely by gateway 102 and/or remote monitoring center 106 (or similar platform separate from the local medical device 100). Non-invasive monitoring of AGEs concentration levels relies on one or more optical sensors positioned on the medical device to provide one or more excitation sources (e.g., light) to patient tissue and monitor the emission response (e.g., light emitted by the patient tissue as a result of reflection, fluorescence, absorbance of the incident light). For example, in one embodiment one or more light sources associated with the medical device direct incident light to patient tissue. In addition, one or more photodetectors associated with the medical device receives light emitted from the patient at a particular emission wavelength associated with the photodetector. The photodetector converts the measured emission (i.e., optical signal) to an electrical signal that is representative of the amplitude or strength of the emitted light. As discussed in more detail below, analysis of the detected optical signal can be utilized to monitor AGE concentration levels such as HbA1c. In some embodiments, the analysis is performed locally by the medical device 100 or 110, while in other embodiments the monitored optical signal is transmitted to a gateway 102 or remote center 106 for analysis to detect concentration levels in blood.

In one embodiment, gateway 102 comprises components of the zLink™, a small portable device similar to a cell phone that wirelessly transmits information received from medical device 100 to remote monitoring center 106. The gateway 102 may consist of multiple devices, which can communicate wired or wirelessly with remote center 106 in many ways, for example with a connection 104 which may comprise an Internet connection and/or with a cellular connection. Remote center 106 may comprise a hosted application for data analysis and storage that also includes a website, which enables secure access to physiological trends and clinical event information for interpretation and diagnosis. Remote center 106 may further or alternatively comprise a back-end operation where physiological data from adherent devices 100 or 110 are read by human experts to verify accuracy. Reports may then be generated at remote monitoring center 106 for communication to the patient's physician or care provider. As discussed above, in other embodiments gateway 102 may be implemented with a user device such as a smartphone, tablet, or computer capable of storing and executing one or more applications capable of processing data received from medical devices 100 and/or 110, as well as communicating the received data to remote monitoring center 106.

In an exemplary embodiment, the monitoring system comprises a distributed processor system with at least one processing module (not shown) included as part of adherent device 100 and/or 110, at least one processor 102P of gateway 102, and at least one processor 106P at remote center 106, each of which processors can be in electronic communication with the other processors. At least one processor 102P comprises a tangible medium 102T, and at least one processor 106P comprises a tangible medium 106T. Remote processor 106P may comprise a backend server located at the remote center. Physiological parameters—including optical signals—monitored by medical device 100 and/or 110 may be analyzed by one or more of the distributed processors included as part of medical device 100 and/or 110, gateway 102, and/or remote monitoring center 106.

Figure 2A:
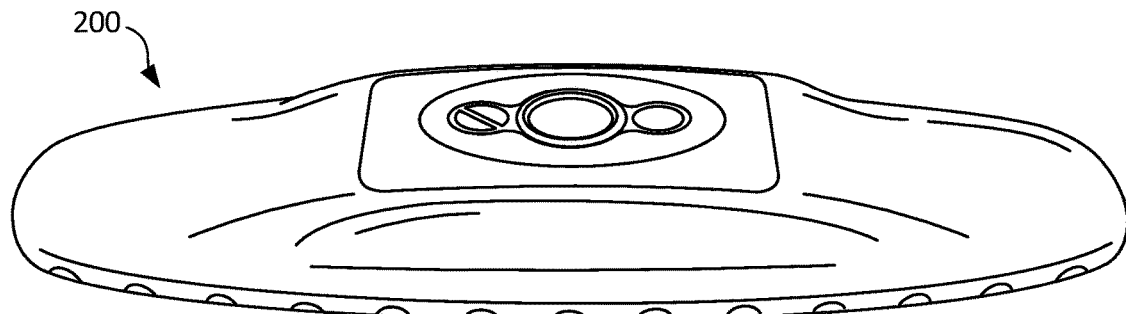
FIGS. 2A-2C are perspective views of an adherent monitoring device according to some embodiments.
Figure 2B:
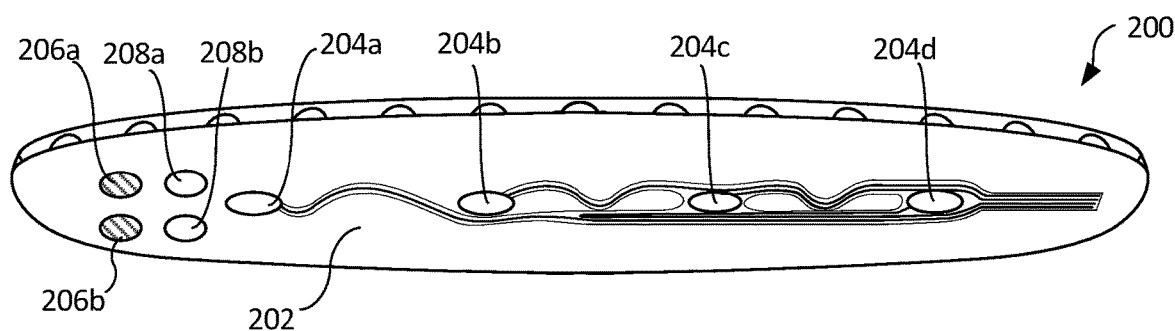
Figure 2C:
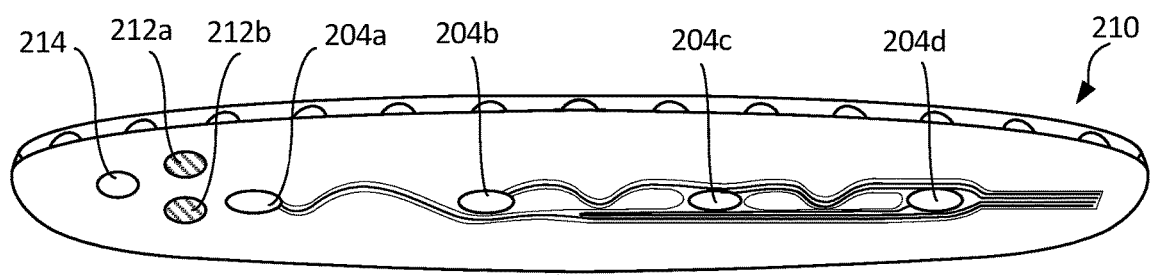

FIGS. 2A-2C are perspective views of an adherent monitoring device according to some embodiments. Adherent devices are adhered to the skin of a patient, and include one or more sensors utilized to monitor physiological parameters of the patient. Adherent devices are often-times utilized for long-term monitoring of ambulatory patients, allowing physiological parameters of the patient to be monitored over a period of time (e.g., days, weeks, months). Adherent devices therefore allow for both long-term monitoring of patients with chronic conditions (e.g., diabetes, heart failure) as well as monitoring and detection of acute incidences (e.g., carbon monoxide poisoning), and can be utilized to provide dynamic monitoring (e.g., monitoring in response to a trigger or detected condition). This is in contrast with typical blood/tissue tests, which require blood be drawn by a lab and therefore do not allow for either long-term monitoring or detection of acute conditions.

The adherent device 200 illustrated in FIG. 2A illustrates the relatively low profile of adherent devices, which allows patients to wear the devices comfortably over a long period of time.

In the embodiment shown in FIG. 2B, a bottom surface 202 of adherent device 200 is shown, which includes a plurality of electrodes 204a-204d, first and second light emitters 206a and 206b, and first and second photodetectors 208a, 208b. Electrodes 204a-204d are utilized to monitor electrical activity associated with the patient, including monitoring electrocardiogram (ECG) information and bio-impedance. First and second light emitters 206a and 206b are utilized to generate excitation signals (e.g., incident light) at first and second excitation wavelengths. Depending on the particular AGE protein and/or lipid to be monitored (e.g., HbA1c), different wavelengths of light may be selected in order to generate a particular emission response, which refers to how the incident light at a particular wavelength interacts with the AGE protein or lipid via reflectance, absorbance, fluorescence, etc., which is represented by the light emitted from the patient. For example, hemoglobin (Hb) is defined by an emission response to incident light provided at a particular wavelength. Similarly, glycated hemoglobin (HbA1c) is defined by an emission response to incident light provided at a different wavelength. In some embodiments, first and second excitation wavelengths are selected to generate significant emission responses for the particular protein and/or lipid being targeted for monitoring.

In addition, the embodiment shown in FIG. 2B, the bottom surface 202 of adherent device 200 includes two or more photodetectors 208a, 208b. In this embodiment, each photodetector is configured to detect light at a particular emission wavelength. The wavelength selected is based on the emission response of the AGE protein/lipid being monitored (e.g., HbA1c, etc.). In a lab environment, the entire spectral response (e.g., all wavelengths) may be measured and analyzed. This is cost prohibitive though in an adherent device. Instead of monitoring all wavelengths, the embodiment shown in FIG. 2B selects one or more wavelengths to monitor. The wavelengths are selected based on the particular AGE protein/lipid being analyzed, and are selected to correlate with either maximums or significant minimums associated with the AGE emission response being monitored For example, hemoglobin is defined by an emission response morphology that includes a maximum at a wavelength of approximately 575 nm, and a minimum at wavelengths greater than 560 nm. In this example, photodetector 208a may be configured to monitor an attribute (e.g., amplitude) of the emission response provided at a wavelength of 575 nm, and photodetector 208b may be configured to monitor an attribute (e.g., amplitude) of the emission response provided at a wavelength of 560 nm. As discussed below, the ratio of the maximum measurement to minimum measurement are utilized to determine the concentration of the targeted AGE protein/lipid. In other embodiments, one photodetector 208a is configured to monitor an emission wavelength associated with a maximum associated with a first protein/lipid (e.g., hemoglobin (Hb) and photodetector 208b is configured to monitor an emission wavelength associated with a maximum associated with a second protein/lipid (HbA1c). In this embodiment, the ratio of the maximum measurement associated with a first targeted protein/lipid to the maximum measurement associated with a second targeted protein/lipid are utilized to determine the concentration of the targeted AGE protein/lipids relative to one another. In another embodiment, photodetectors 208*a* and/or 208*b* may be utilized to monitor first and second temporal attribute of the emission response (e.g., average amplitude over a period of time, rate of change, etc.), wherein a ratio is generated based on the first and second temporal attributes to determine the concentration of the targeted AGE protein/lipid relative to one another.

In this way, emission response ratios can be created by selectively applying first and second excitation wavelengths to generate separate first and second emission responses. In other embodiments, the ratio can be created by selectively applying a single excitation wavelength and with respect to the emission response, utilizing a first emission wavelength and second emission wavelength to generate the desired ratio.

Based on the measured attribute of emitted light at select wavelengths, a ratio of the measured attributes is calculated, wherein the ratio provides a measure of the AGE protein/lipid concentration. A benefit of utilizing a ratio is that the measure is relatively immune to noise and external factors such as change in ambient light intensity, molecule concentrations, artifacts, light source instability, detector instability, and/or changes in placement of the sensor. For example, a measurement taken during the night in which little or no external light is available may provide an amplitude that is much lower than the amplitude measured if the patient is outside in the sun—in which light from the sun increases the measured amplitude at both the minimum and the maximum.

Although in the embodiment shown in FIG. 2B, a pair of emitters 206*a* and 206*b* is shown along with a pair of detectors 208*a* and 208*b*, additional emitters may be utilized along with additional detectors. In addition, although each emitter and detector is illustrated as a separate entity, in some embodiments the functions of an emitter and detector are included in a single device. Therefore, on one embodiment light source 206 may also include a photodetector 208. Photodetectors may be implemented with well-known imaging sensors such as CCD or CMOS image sensors.

In the embodiment shown in FIG. 2C, rather than utilize a two or more detectors, adherent device 210 includes a single photodetector 214. In this embodiment, each light source or emitter 212*a* and 212*b* once again provides incident light at a unique wavelength selected to generate an emission response related to the AGE protein/lipid to be monitored. Photodetector 214 monitors emissions at a single wavelength, selected to correspond with a maximum of the emission response associated with the first excitation wavelength or the second excitation wavelength. For example, in one embodiment the first excitation wavelength is selected to provide a significant (e.g. maximized) first emission response associated with AGE proteins, and wherein the second excitation wavelength is selected to provide a significant minimum emission response from the same AGE protein/lipid (e.g., HbA1c). The photodetector 214 monitors the respective emission responses at a wavelength selected to correspond with a maximum of the first emission response and a significant minimum of the second emission response. In this embodiment, selective variation of the excitation wavelength creates the desired difference/ratio in the emission response.

In some embodiments, emitters 212*a* and 212*b* are controlled to generate incident light mutually exclusive of one another (e.g., one at a time). This allows detector 214 to measure the emission response associated with the first excitation wavelength and the emission response associated with the second excitation wavelength, separately. For example, in one embodiment emitter 212*a* is activated to provide incident light at a first excitation wavelength. Photodetector 214 measures an attribute (e.g., amplitude) relating to the emission response at a given emission wavelength. Subsequently, emitter 212*a* is deactivated and emitter 212*b* is activated to provide incident light at a second excitation wavelength. Photodetector 214 measures the attribute (e.g., amplitude) relating to the emission response at the same given emission wavelength. The ratio of the measured amplitudes is utilized to measure a blood concentration component and or a blood concentration component level (e.g., Hg) relative to another blood concentration level (e.g., HbA1c).

In other embodiments, more than two light sources (e.g., emitters) may be utilized to provide incident light at more than two unique excitation wavelengths. In addition, more than a single photodetector may be utilized in order to measure attributes of the emission response at a plurality of emission wavelengths. Similarly, although a pair of emitters 212*a* and 212*b* and a single photodetector 214 are utilized in FIG. 2C, in other embodiments more than two emitters may be utilized along with a plurality of photodetectors. In addition, although each emitter and photodetector is illustrated as a separate entity, in some embodiments the functions of an emitter and photodetector are included in a single element.

Figure 3:
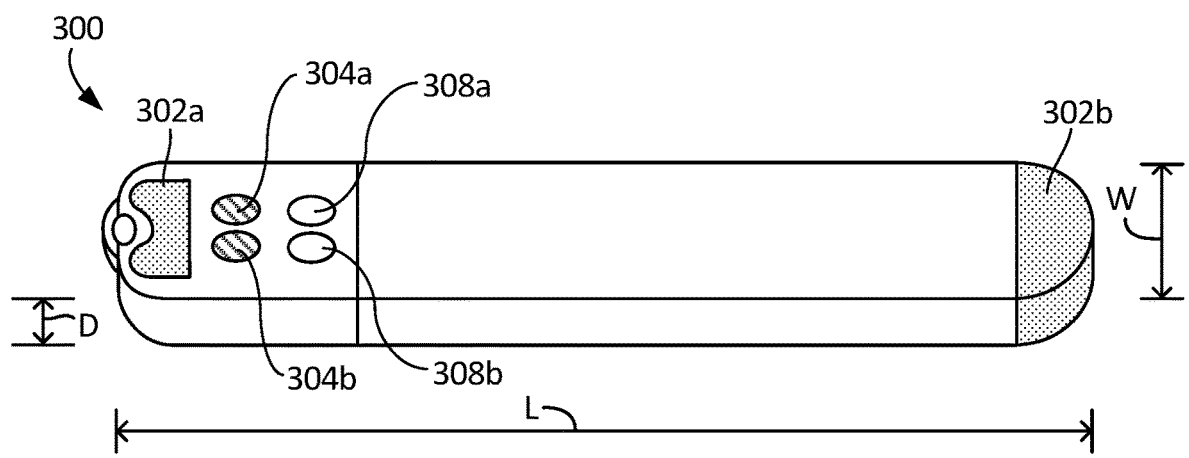
FIG. 3 is a perspective view of an insertable monitoring device according to some embodiments.

FIG. 3 is a perspective view of an insertable monitoring device 300 according to some embodiments. In contrast with an adherent device, which is secured to the skin of a patient, insertable monitoring devices 300 are inserted subcutaneously. Insertable device 300 includes at least first and second electrodes 302*a* and 302*b*, at least one light emitter 304 (emitters 304*a* and 304*b* are shown) and at least one photodetector 308 (photodetectors 308*a* and 308*b* are shown). As discussed above with respect to FIGS. 2B and 2C, insertable monitoring device 300 utilizes the at least one emitter to emit light at an excitation wavelength selected based on the AGE protein/lipid to be monitored (e.g., HbA1c). The at least one photodetector 308 may be utilized to monitor one or more emission wavelengths, selected to correlate with maximums and/or minimums of the AGE protein/lipid to be monitored (e.g., maximum associated with Hb and maximum associated with HbA1c). As described with respect to FIGS. 2A-2C, emission response ratios can be created by selectively applying first and second excitation wavelengths to generate separate first and second emission responses. In other embodiments, the ratio can be created by selectively applying a single excitation wavelength and with respect to the emission response, utilizing a first emission wavelength and second emission wavelength to generate the desired ratio.

For example, in one embodiment insertable monitoring device 300 is configured to generate light at a first excitation wavelength selected to generate an emission response having a maximum responsive to an AGE protein/lipid, and measures the emission response at a wavelength that corresponds with a maximum (peak) of the emission response. In addition, monitoring device 300 generates light at a second excitation wavelength selected to generate an emission response having a maximum responsive to a second protein/lipid (e.g., AGE protein/lipid or non-AGE protein/lipid such as hemoglobin (Hb)). An emission response to the second excitation wavelength is measured at a wavelength that corresponds with a maximum (peak) of the emission response (same or different wavelength as that utilized for monitoring the first AGE protein/lipid). A ratio is calculated based on a first emission response monitored with respect to the first excitation wavelength and a second emission response monitored with respect to the second excitation wavelength (wherein the first and second emission response may be at the same emission wavelength or unique emission wavelengths). For example, in one embodiment the AGE protein/lipid selected by the first excitation wavelength is glycated hemoglobin (HbA1c) and the second protein/lipid selected by the second excitation wavelength is hemoglobin (Hb), such that the ratio describes the relationship between concentration of HbA1c and Hb, which is useful in monitoring the progression of conditions such as pre-diabetes or diabetes.

In another embodiment, monitoring device 300 is configured to generate light at a first excitation wavelength selected to generate a first emission response having a maximum responsive to a selected AGE protein/lipid (e.g., HbA1c), and to generate light at a second excitation wavelength selected to generate a second emission response having a minimum responsive to the same AGE protein/lipid (e.g., HbA1c). The respective emission responses are measured at an emission wavelength corresponding with the maximum (peak) of the first emission response, wherein the ratio provides an assessment of the selected AGE protein/lipid concentration, but not relative to any other protein.

In another embodiment, monitoring device 300 is configured to generate light at a first excitation wavelength selected to generate an emission response having a maximum response to a selected AGE protein/lipid, and measures the emission response at a first wavelength that corresponds with a maximum (peak) of the emission response and at a second wavelength that corresponds with a minimum of the emission response. The ratio provides an assessment of the AGE protein/lipid concentration.

In another embodiment, any of the above embodiments may be utilized in conjunction with measurements of autofluorescence lifetimes associated with the respective emission responses. For example, a first excitation wavelength is selected to generate a first emission response having a maximum responsive to a selected AGE protein/lipid, wherein an autofluorescence lifetime is measured with respect to the emission response. A second excitation wavelength is selected to generate a second emission response having a minimum responsive to the same AGE protein/lipid, and an autofluorescence lifetime is measured with respect to the emission response. The ratio of the autofluorescence lifetimes is utilized to determine the concentration of AGE protein/lipid associated with the tissue.

Figure 4:
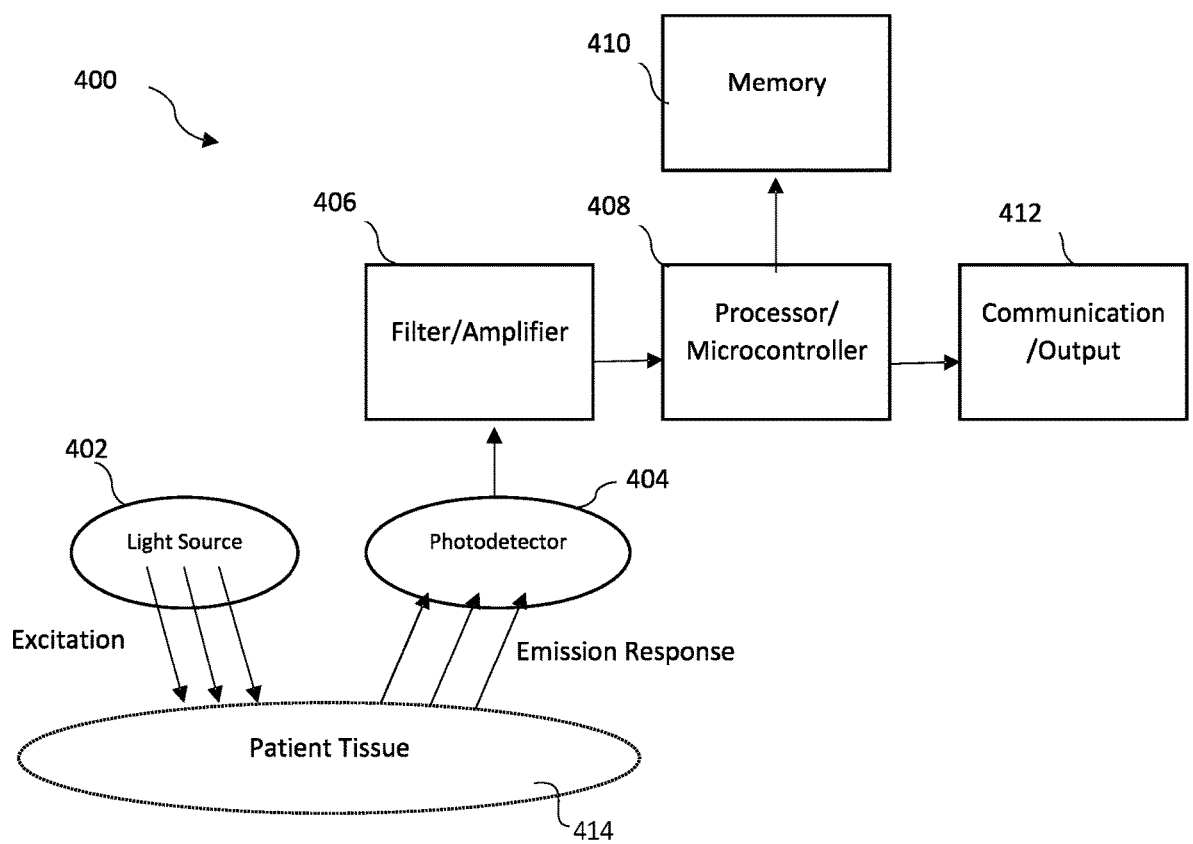
FIG. 4 is a block diagram illustrating components utilized to monitor optical signals and processing optical signals according to some embodiments.

FIG. 4 is a block diagram illustrating components utilized to monitor optical signals and processing optical signals according to some embodiments.

Medical device 400 includes at least one light source 402, at least one detector 404, filter/amplifier 406, processor/microcontroller 408, memory 410, and communication/output 412. As described above, medical device 400 may be adhered to the patient's skin, clipped onto a patient's finger, attached via an arm cuff, inserted subcutaneously, or implanted within the patient. Light source 402 emits light that is provided incident to the patient's tissue, referred to herein as "excitation". In some embodiments, excitation may be provided at a plurality of wavelengths or at a selected wavelength. For example, the wavelength of the emitted light may be selected based on the AGE protein/lipid (e.g., particular protein) to be analyzed, wherein different wavelengths of light interact differently with particular proteins/lipids. In some embodiments, light source 402 includes a plurality of light sources each capable of emitting at a particular unique wavelength.

Light from light source 402 interacts with patient tissue 414. The interaction is a result of one or more processes, including autofluorescence, absorption, and reflectance that results in the emission of light from the tissue, referred to as the emission response. The emission response is detected by the one or more photodetectors 404. In some embodiments, photodetector 404 may utilize well-known optical sensors, such as complimentary metal-oxide-semiconductor (CMOS) sensor or a charge-coupled device (CCD) sensor. Each of the one or more photodetectors 404 is configured to detect light at a particular emission wavelength. For embodiments in which a plurality of emission wavelengths are monitored, a plurality of photodetectors 404 are required, each configured to monitor one of the desired emission wavelengths. The emission wavelengths monitored by the one or more photodetectors 404 are selected based on the particular AGE protein/lipid (e.g., HbA1c) being monitored. For example, the emission response morphology (i.e., amplitude of the emission response across the entire wavelength spectrum) depends on how light interacts with the AGE protein/lipid being monitored, with emission responses for each blood component providing different emission response morphology. In particular, emission wavelengths monitored by the one or more photodetectors are selected to correspond with maximum and/or minimum values associated with the emission response spectrum being monitored.

The one or more photodetectors convert the monitored optical signal (i.e., the emission response) to an electrical signal representative of the amplitude of the emission wavelength being monitored. Filter/amplifier 406 filters and amplifies the signal to provide a clean signal to processor/microcontroller 408.

Processor/microcontroller 408 operates in conjunction with memory 410 and communication output 412. In some embodiments, processor/microcontroller 408 provides the measured emission response signals monitored by the photodetectors to an intermediate gateway 102 and/or remote monitoring center 106 (shown in FIG. 1) for subsequent processing. In other embodiments, processor/microcontroller 408 executes instructions locally to perform analysis on the monitored emission response. This may include calculating ratios associated with two or more monitored emission responses, calculating blood component concentrations based on the calculated ratios, comparing the ratios and/or blood component concentrations to threshold values, and/or storing calculated ratios and/or blood component concentrations to memory 410. Results of any analysis performed locally by processor/microcontroller may then be communicated to intermediate device 102, gateway 106, or provided as an alert to the patient (e.g., audio alert).

Figure 5:
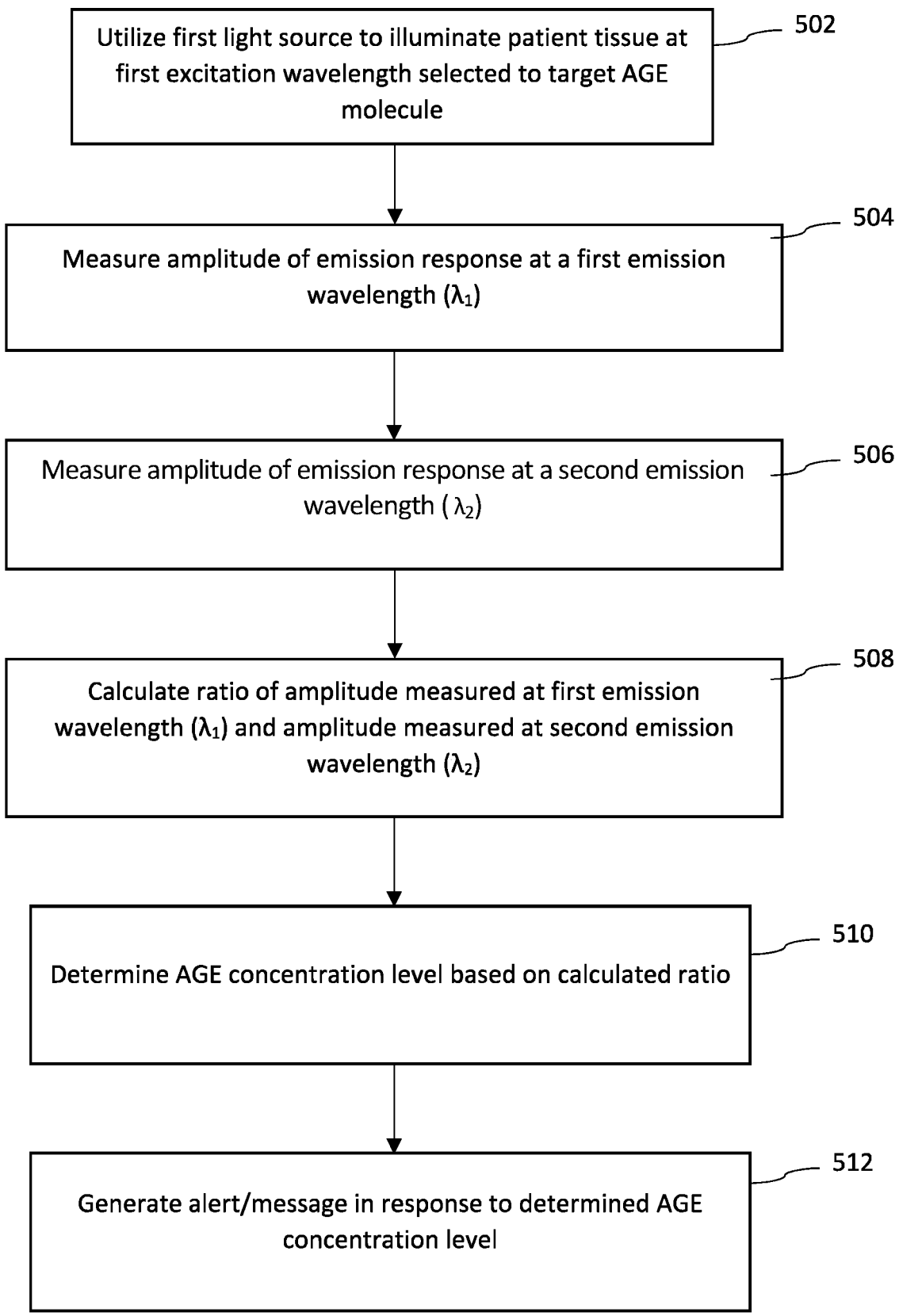
FIG. 5 is a flowchart that illustrates steps utilized to measure advanced glycation end-products (AGE) according to an embodiment of the present invention.
Figure 6:
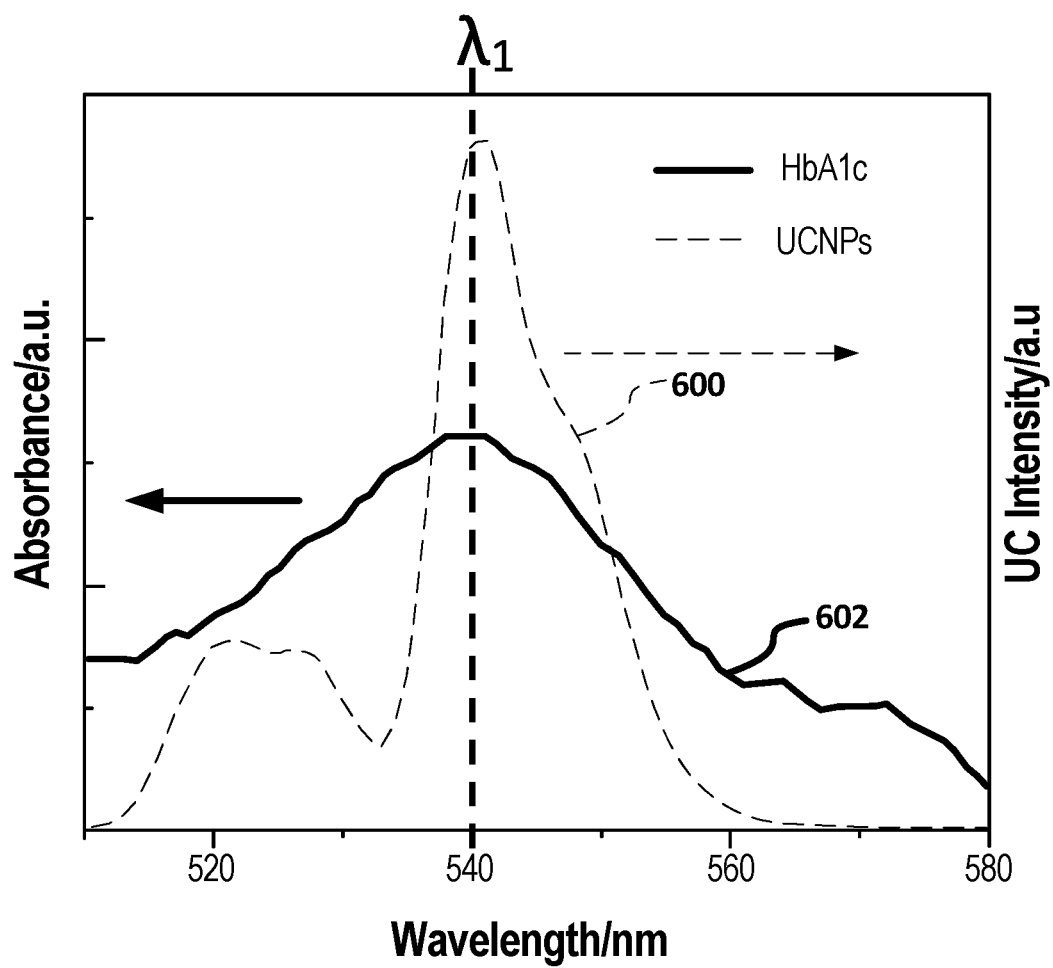
FIG. 6 is a graph that illustrates relative absorbance of HbA1c at various wavelengths.

FIG. 5 is a flowchart that illustrates steps utilized to measure AGEs protein/lipid/enzyme according to embodiments of the present invention. Reference is made to FIG. 6, which is a graph illustrating relative absorbance (lefty-axis) of a particular AGE protein (e.g., HbA1c) at various wavelengths (line 602) as compared with the fluorescence intensity (righty-axis) of upconversion nanoparticles (UNCPs) (line 600), and FIG. 7, which is a graph illustrating the relationship between intensity of the measured emission responses as it relates to varying concentration levels of HbA1c. As illustrated in FIG. 6, HbA1c molecules exhibit relatively high absorption at a wavelength of approximately 541 nm ($\lambda_1$ in FIG. 6), while UNCP exhibit relatively high intensity emissions at approximately the same wavelength. Thus, as the concentration of HbA1c molecules increases relative to the number of UNCP particles, light absorbance increases and emitted intensity decreases, resulting in an expected decline in intensity as HbA1c concentration levels increase. This is confirmed in FIG. 7, which illustrates that an increase in HbA1c concentration results in a decrease in intensity of monitored light at the mission wavelength of 541 nm. These characteristics of glycated hemoglobin (HbA1c) are utilized in the embodiment described with respect to FIG. 5.

Figure 7:
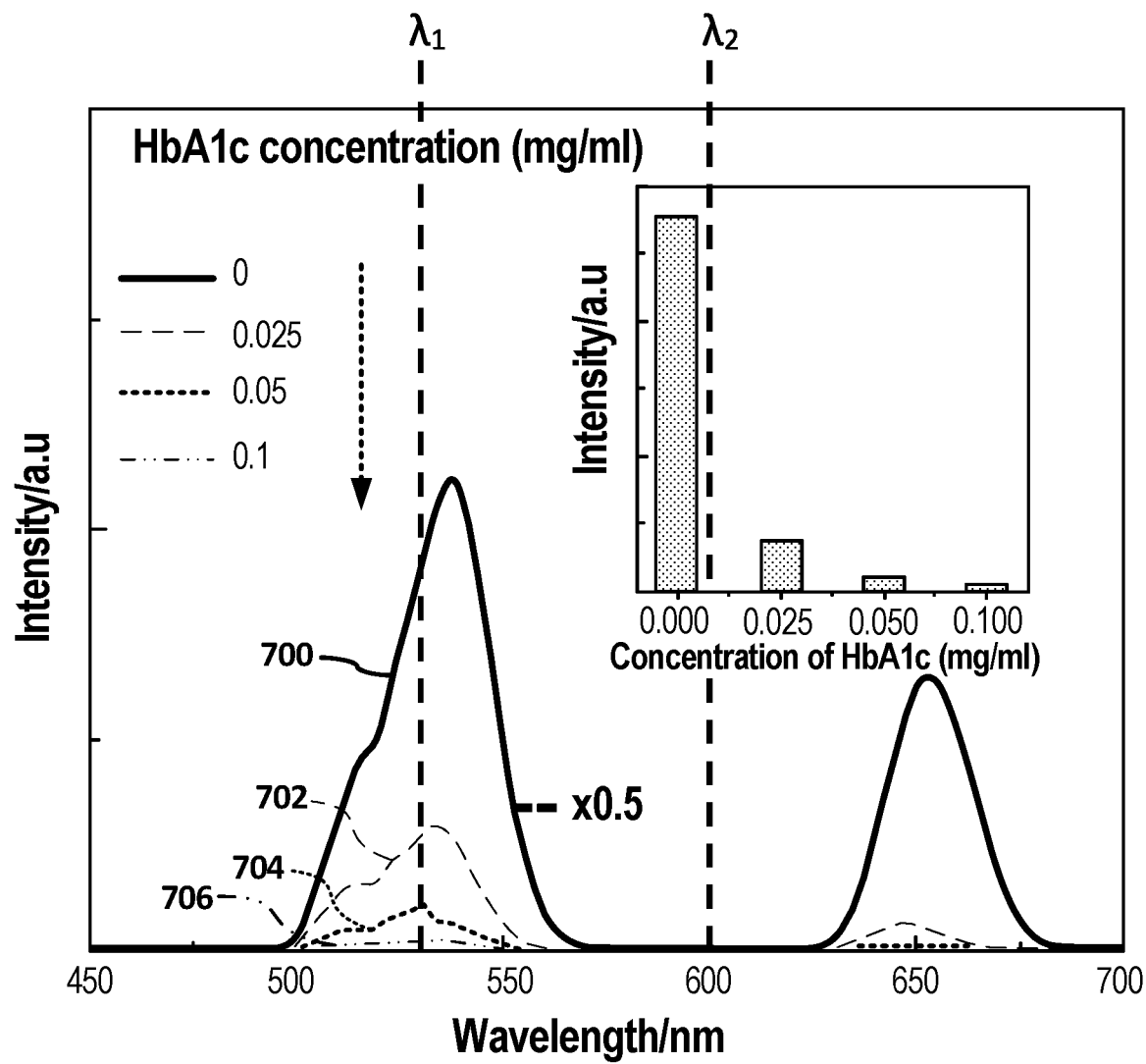
FIG. 7 is a graph that illustrates the relationship between emission response intensity and HbA1c concentration.

At step 502, a light source is utilized to provide excitation to patient tissue at a first excitation wavelength selected to target selected AGE molecules (HbA1c in the example shown in FIGS. 6 and 7). For example, in one embodiment the excitation wavelength of the first light source is in the infrared range (e.g., 700 nm to approximately 1 micron or µm), although in other embodiments other excitation wavelengths (e.g., visible, ultra-violet spectrum) may be utilized so long as the emission response provides the desired morphology. In one embodiment, the excitation wavelength is equal to approximately 980 nm, which provides the emission response morphology illustrated in FIG. 6, which includes the emission response of HbA1c as well as UNCPs. In other embodiments, depending on the type of AGE molecule to be targeted, the excitation wavelength is modified to provide an emission response responsive to the targeted AGE molecule.

At step 504, in response to the excitation signal, a first emission response is generated and monitored by one or more of the photodetectors at a first emission wavelength $\lambda_1$. That is, rather than monitor the entire spectrum of wavelengths associated with the emission response, a particular wavelength is selected for monitoring. As discussed above, monitoring the entire spectrum of wavelengths is cost-prohibitive both in terms of the number of detectors required and processing power required. The emission wavelength selected corresponds with a maximum of the targeted AGE molecule (e.g., HbA1c). In the embodiment shown in FIGS. 6 and 7, the first emission wavelength is equal to approximately 540 nm. As illustrated in FIGS. 6 and 7, the intensity of the emission response measured at this wavelength depends, at least in part, on the concentration of targeted AGE molecules (in this case, HbA1c), but also on the external factors such as placement of the medical device, ambient light, etc. To isolate the impact of the AGE molecules on the emission response, a second emission response is monitored at a minimum of the emission response.

At step 506, absorption/intensity of the emission response is measured at a second emission wavelength corresponding with a minimum of the targeted emission response. For example, FIG. 7 illustrates that with respect to the HbA1c molecule, local maximums exist at wavelengths of approximately 541 nm and 650 nm, but a minimum is provided at a wavelength of approximately 600 nm. In this embodiment, the second emission wavelength is selected at this wavelength to serve as the emission response minimum or reference. As indicated, other wavelengths may be selected to represent a minimum of the emission response, including wavelengths less than 500 nm, greater than approximately 675 nm, and between approximately 560 nm and approximately 630 nm. The amplitude of the emission response measured at the second wavelength (e.g., minimum of the emission response) should not vary with changes in the concentration of the targeted AGE molecule. However, the amplitude measured at the second wavelength may vary based on external factors such as ambient light, location of the device on the patient's body, etc. Utilizing a ratio comprised of an emission response associated with a maximum and an emission response associated with a minimum or reference has the effect of canceling the external factors unrelated to the concentration of the targeted AGE molecule.

At step 508, a ratio of the amplitude measured at the first emission wavelength and amplitude measured at the second emission wavelength is calculated. For example, in one embodiment the ratio is defined as the maximum emission response divided by the minimum emission response.

At step 510, the concentration of the targeted AGE molecule is determined based on the calculated ratio. As illustrated with respect to FIG. 7, the intensity/amplitude of HbA1c emission response decreases as the concentration of HbA1c increases. For example, FIG. 7 illustrates emission response for HbA1c concentration levels of zero (line 700), 0.025 (line 702), 0.05 (line 704), and 0.1 (line 706), with each increase in HbA1c concentration resulting in a decrease in the amplitude of the emission response. As a result, the ratio (as defined above, in which the maximum emission response is divided by the minimum emission response) decreases as the HbA1c concentration increases. In other embodiments, the ratio may be inverted such that as the HbA1c concentration increases, the ratio increases. The monitored concentration of HbA1c is utilized to monitor the risk of diabetes.

At step 512, alerts/messages are generated in response to the calculated HbA1c level. For example, in embodiments in which the ratio calculation and calculation of the HbA1c level is done locally on the medical device 100 and/or 110, an audio and/or visual alert may be provided to the patient directly indicating the calculated HbA1c level. In addition, the calculated HbA1c level may be communicated to a remote monitoring center for provision to the patient's physician. In other embodiments, the ratio calculation and calculation of HbA1c levels are done remotely. In response to the ratio exceeding or falling below a defined threshold, an alert may be communicated to the patient's physician or may be communicated to the patient via a messaging system.

Although in the embodiment described with respect to FIG. 5, separate excitation wavelengths were utilized in combination with monitoring a constant emission response wavelength, in other embodiments the excitation wavelength may remain constant and two or more emission wavelengths are monitored to generate the desired ratio, wherein the emission wavelengths are selected to correspond with a maximum value associated with the emission response and a minimum or reference value associated with the emission response.

Figure 8:
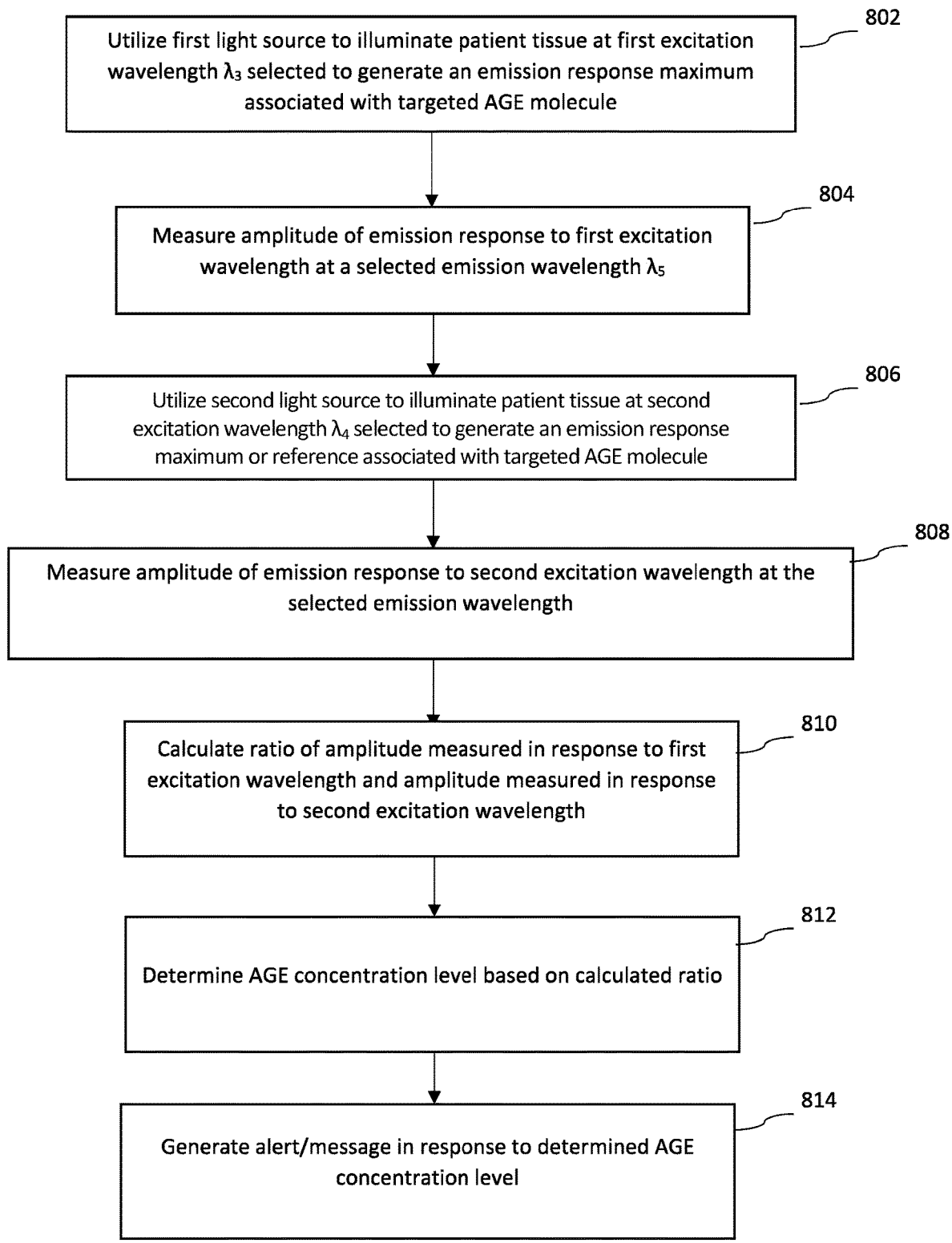
FIG. 8 is flowchart that illustrates steps utilized to measure advanced glycation end-products (AGE) according to another embodiment of the present invention.

FIG. 8 is a flowchart that illustrates steps utilized to measure AGEs protein/lipid/enzyme according to an embodiment of the present invention. In contrast with the embodiment described with respect to FIG. 5, the embodiment shown in FIG. 8 utilizes first and second excitation wavelengths to excite the tissue being monitored and to generate first and second emission responses.

At step 802, a light source is utilized to provide excitation to patient tissue at a first excitation wavelength selected to target selected AGE molecules (e.g., HbA1c). For example, in embodiments relying on autofluorescence spectroscopy, the excitation wavelength may be selected to correspond with the maximum autofluorescence response of the selected AGE molecule. In the embodiment shown in FIG. 9, this maximum occurs at a wavelength of approximately 310 nm (e.g., $\lambda_3$). In other embodiments, depending on the type of AGE molecule to be targeted and the type of spectroscopy being performed, the excitation wavelength is modified to provide an emission response responsive to the targeted AGE molecule.

At step 804, in response to the excitation signal, a first emission response is generated and monitored by one or more of the photodetectors at a first emission wavelength $\lambda_5$. That is, rather than monitor the entire spectrum of wavelengths associated with the emission response, a particular wavelength is selected for monitoring. As discussed above, monitoring the entire spectrum of wavelengths is cost-prohibitive both in terms of the number of detectors required and processing power required. The emission wavelength selected corresponds with a maximum of the emission response corresponding with the targeted AGE molecule (e.g., HbA1c). In the embodiment shown in FIG. 9, the selected emission wavelength is equal to approximately 345 nm. When relying on autofluorescence spectroscopy, the excitation wavelength selected to target a particular AGE protein is typically lower than the corresponding emission wavelength, as the AGE molecules absorb energy at a lower wavelength and emit (e.g., autofluorescence) at a higher wavelength.

At step 806, a light source is utilized to provide excitation to patient tissue at a second excitation wavelength selected to minimize the emission response associated with the targeted AGE molecules (e.g., HbA1c). In the embodiment shown in FIG. 9, the minimum corresponds with a wavelength of approximately 320 nm ($\lambda4$). That is, providing excitation at this wavelength should not result in the absorption of light by the targeted AGE molecules and therefore should result in an emission response that is minimized.

Figure 9:
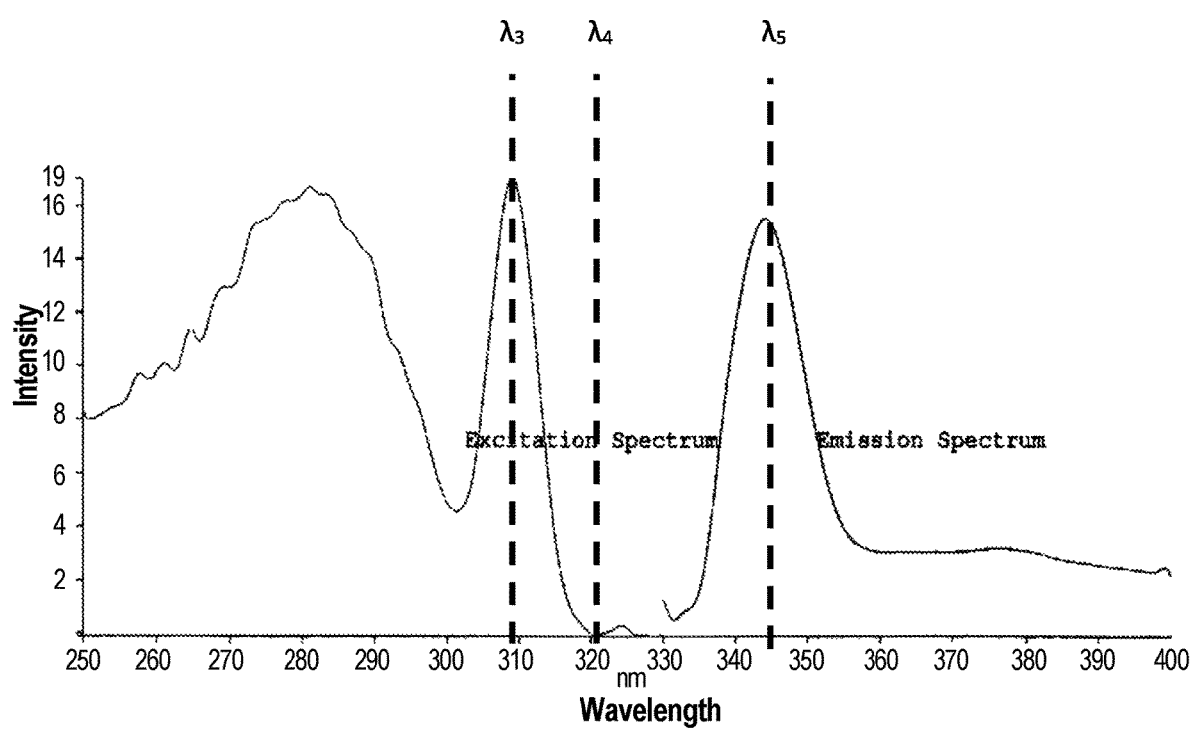
FIG. 9 is a graph that illustrates the excitation spectrum and emission spectrum for HbA1c concentrations.

At step 808, in response to the second excitation signal provided at the second excitation wavelength, a second emission response is generated and monitored by one or more of the photodetectors at a first emission wavelength $\lambda_5$. That is, in this embodiment the emission response to the first and second excitation signal is monitored at the same emission wavelength. As shown in FIG. 9, the selected emission wavelength is equal to approximately 345 nm. However, because the excitation wavelength is selected to minimize the emission response associated with the targeted AGE molecule, high concentrations of the targeted AGE molecule will not autofluoresce in response to the second excitation wavelength and therefore the monitored amplitude of the emission response will be lower in amplitude than that measured with respect to the first excitation wavelength.

At step 810, a ratio of the emission response measured in response to the first excitation wavelength and the emission response measured in response to the second excitation wavelength is calculated. For example, in one embodiment the ratio is defined as the maximum emission response divided by the minimum emission response.

At step 812, the concentration of the targeted AGE molecule is determined based on the calculated ratio. In one embodiment, the intensity/amplitude of the first emission response increases in response to increased AGE concentrations (e.g., increased autofluorescence response). Similarly, the intensity/amplitude of the second emission response remains approximately the same despite variations in the targeted AGE concentration. As a result, in this embodiment the ratio (as defined above, in which the maximum emission response is divided by the minimum emission response) increases as the AGE concentration increases. In other embodiments, the ratio may be inverted such that as the AGE concentration increases, the ratio decreases.

At step 814, alerts/messages are generated in response to the calculated AGE concentration level. For example, in embodiments in which the ratio calculation and calculation of the AGE concentration level is done locally on the medical device 100 and/or 110, an audio and/or visual alert may be provided to the patient directly indicating the calculated AGE concentration level. In addition, the calculated AGE concentration level may be communicated to a remote monitoring center for provision to the patient's physician. In other embodiments, the ratio calculation and calculation of AGE concentration levels are done remotely. In response to the ratio exceeding a defined threshold, an alert may communicated to the patient's physician or may be communicated to the patient via a messaging system.

Figure 10:
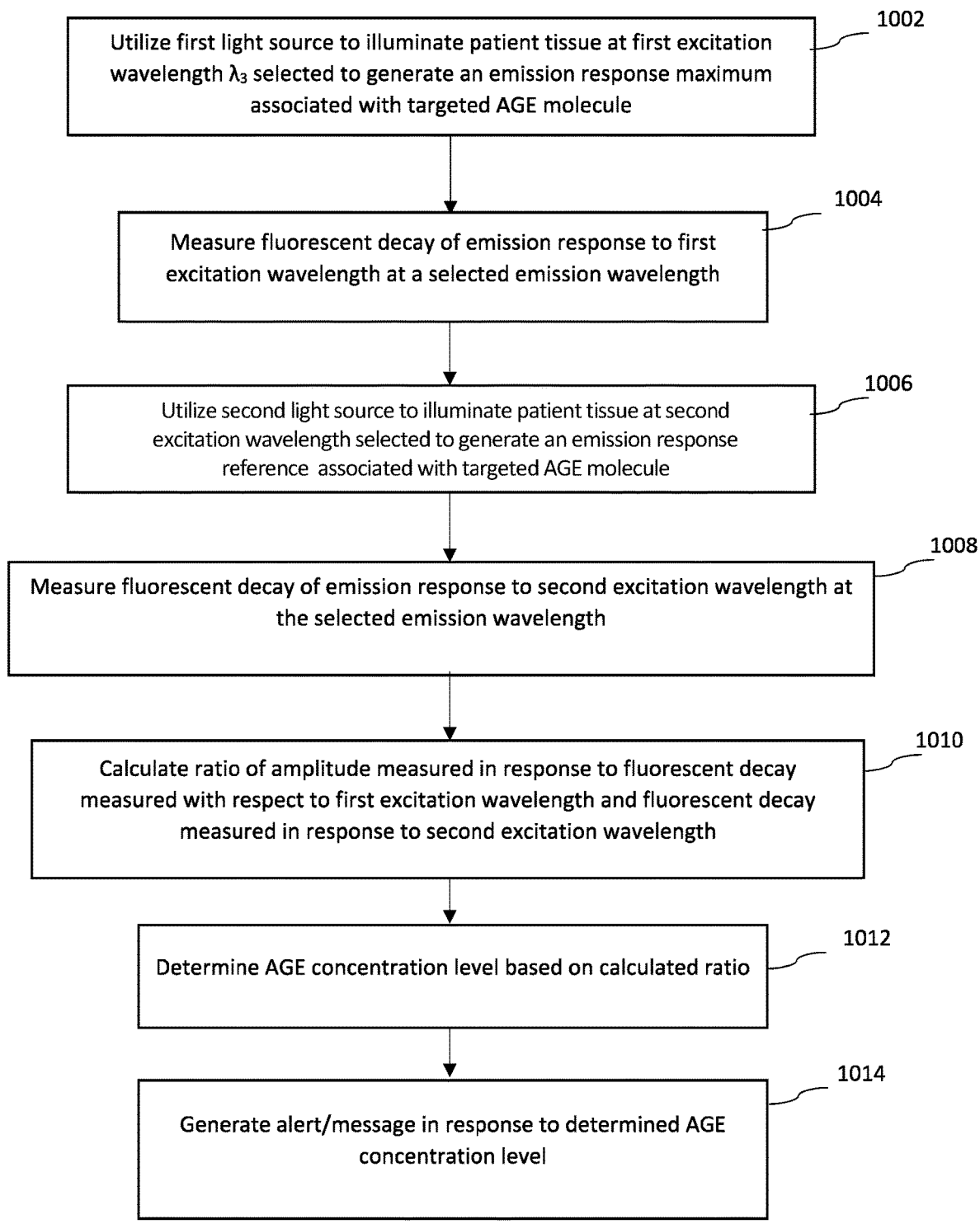
FIG. 10 is flowchart that illustrates steps utilized to measure advanced glycation end-products (AGE) utilizing fluorescent decay according to another embodiment of the present invention.
Figure 11:
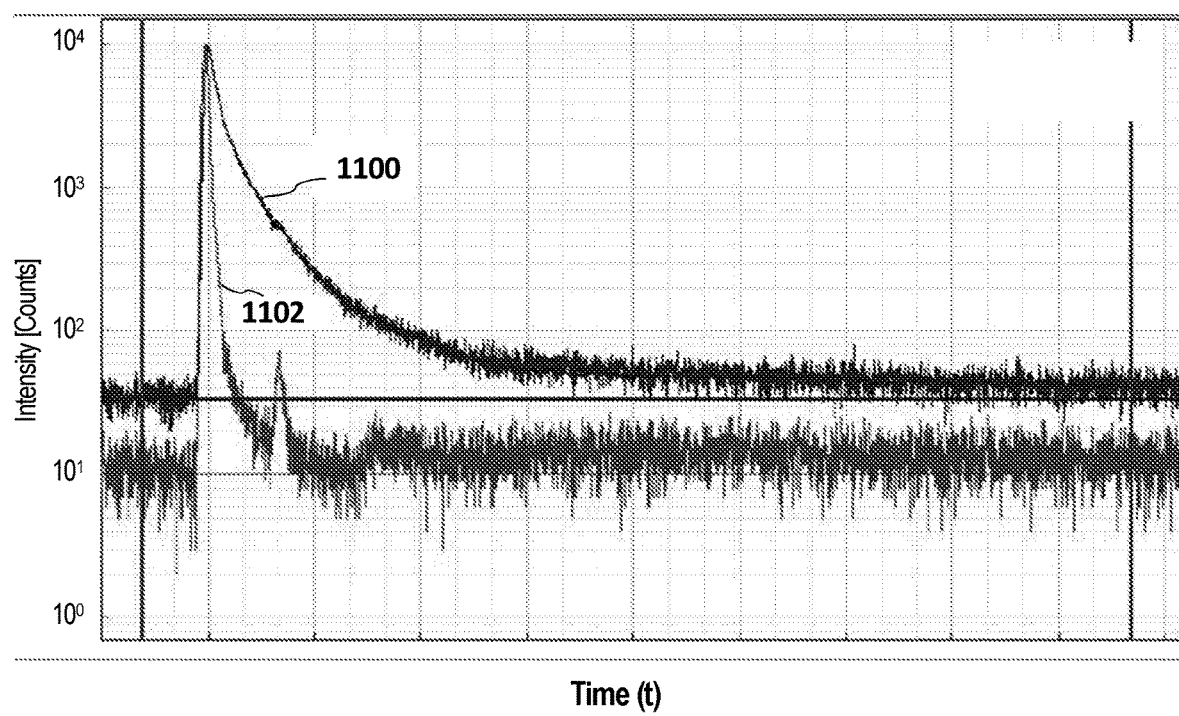
FIG. 11 is a graph that illustrates the autofluorescent decay for HbA1c.

FIG. 10 is a flowchart that illustrates steps utilized to measure AGEs protein/lipid/enzyme according to another embodiment of the present invention. In contrast with the embodiment described with respect to FIGS. 5 and 8, the embodiment shown in FIG. 10 utilizes first and second excitation wavelengths to excite the tissue being monitored and to generate first and second emission responses. Fluorescent decay of the emission responses are monitored as shown in FIG. 11, and ratios are calculated based on the monitored decay (e.g., time length of decay, average monitored value over defined time period, etc.).

At step 1002, a light source is utilized to provide excitation to patient tissue at a first excitation wavelength selected to target selected AGE molecules (e.g., HbA1c). For embodiments in which fluorescence decay is being monitored, the excitation wavelength is selected to be absorbed by the targeted AGE molecule such that an autofluorescence emission is generated. In the embodiment described with respect to FIGS. 8 and 9, a wavelength of approximately 310 nm was selected as an excitation maximum for glycated hemoglobin (HbA1c). In other embodiments, depending on the type of AGE molecule to be targeted and the type of spectroscopy being performed, the excitation wavelength is modified to provide an emission response responsive to the targeted AGE molecule.

At step 1004, in response to the excitation signal, a first emission response is generated and fluorescent decay of the emission signal is monitored by one or more of the photodetectors at a first emission wavelength. For example, FIG. 11 illustrates the fluorescent decay 1100 of the first emission response over time t. Rather than measure an amplitude/intensity of the emission response at a particular emission wavelength (as described with respect to FIGS. 5-9), in this embodiment the fluorescent decay of the emission response is measured as shown in FIG. 11, in which the amplitude/intensity of the emission response 1100 increases to a maximum in response to the excitation signal and then decays over time t to a steady state value. The emission wavelength selected to measure the fluorescent decay corresponds with a significant (e.g., maximum) associated with the emission response of the selected AGE molecule. In the embodiment shown in FIG. 9, the selected emission wavelength is equal to approximately 345 nm. When relying on autofluorescence spectroscopy, the excitation wavelength selected to target a particular AGE protein is typically lower than the corresponding emission wavelength, as the AGE molecules absorb energy at a lower wavelength and emit (e.g., autofluorescence) at a higher wavelength.

In one embodiment, autofluorescence decay is a measure of the time t it takes for the autofluorescence response to decay to a defined percentage of the maximum or peak. The measured decay is representative of the concentration of selected AGE molecules, with increased decay times indicating an increase in concentration of AGE molecules. In other embodiments, rather than measure a length of time between a determined peak and a decay threshold, the fluorescent decay is quantized by averaging the amplitude/intensity over a period of time and/or integrating the fluorescent decay to generate a value representative of the decay rate.

At step 1006, a light source is utilized to provide excitation to patient tissue at a second excitation wavelength. In one embodiment, the second excitation wavelength is selected to provide a reference emission response associated with the targeted AGE molecules (e.g., HbA1c). For example, as described with respect to FIG. 9 above, the excitation wavelength corresponding with the excitation minimum is equal to approximately 320 nm. That is, providing excitation at this wavelength should not result in the absorption of light by the targeted AGE molecules and therefore should result in an emission response that is minimized, thereby providing a reference emission response to be compared with the first emission response.

In other embodiments, rather than select the second excitation wavelength to correspond with a minimum absorption wavelength of the AGE molecule targeted by the first excitation wavelength, the second excitation wavelength may be selected to correspond with a maximum response of a different molecule (e.g., hemoglobin (Hb)). In this embodiment, the ratio defines the relationship between the concentration of the first targeted AGE molecule and the second targeted molecule (e.g., Hb).

At step 1008, in response to the second excitation signal provided at the second excitation wavelength, a second emission response is generated and fluorescent decay is monitored by one or more of the photodetectors at a first emission wavelength. For example, FIG. 11 illustrates the fluorescent decay 1102 of the first emission response over time t. That is, in this embodiment the emission response to the first and second excitation signal is monitored at the same emission wavelength. As shown in FIG. 9, the selected emission wavelength is equal to approximately 345 nm. However, because the excitation wavelength is selected to minimize the emission response associated with the targeted AGE molecule, high concentrations of the targeted AGE molecule will not autofluoresce in response to the second excitation wavelength and therefore the monitored fluorescent decay of the emission response will be shorter than that measured with respect to the first excitation wavelength. As discussed above, in some embodiments the fluorescent decay is monitored for a period of time and an average and/or integral that quantifies the fluorescence decay is calculated.

In other embodiments, in which the second excitation wavelength is selected to correspond with a different molecule, then at step 1008 a second emission wavelength may be selected that corresponds with the emission response of the different molecule (e.g. Hb) and the fluorescent decay may be measured with respect to the emission response at the second wavelength. Similarly, other methods of quantifying the fluorescent decay may be relied upon as discussed above. As described above, if the second excitation wavelength is selected to correspond with a different molecule, then the ratio calculated at step 1010 represents the relationship between the concentration of the first AGE molecule and the second targeted molecule (e.g., Hb).

At step 1010, a ratio of the fluorescent decays measured in response to the first excitation wavelength and the emission response measured in response to the second excitation wavelength is calculated. As discussed above, if the excitation wavelengths are selected to correspond with a maximum emission response and a minimum emission response of a selected AGE protein/lipid, then the ratio represents the concentration of the selected AGE protein/lipid. If the first and second excitation wavelengths are selected to correspond with different molecules (e.g., HbA1c and Hb, respectively) then the ratio calculated at step 1010 is representative of the relationship between concentration levels of the selected molecules. Depending on the application, one ratio may have benefits over the other.

At step 1012, the concentration of the targeted AGE molecule is determined based on the calculated ratio. In one embodiment, the autofluorescent decay of the first emission response increases in response to increased AGE concentrations (e.g., increased autofluorescence response). Similarly, the autofluorescent decay of the second emission response remains approximately the same despite variations in the targeted AGE concentration. As a result, in this embodiment the ratio (as defined above, in which the maximum emission response is divided by the minimum emission response) increases as the AGE concentration increases. In other embodiments, the ratio may be inverted such that as the AGE concentration increases, the ratio decreases.

In embodiments in which first and second excitation wavelengths are selected to target first and second molecules, then the ratio calculated at step 1012 represents the concentration of the targeted AGE molecule relative to concentration of a different molecule (e.g. Hb). In some embodiments, in which a molecule such as hemoglobin is converted to an AGE molecule (e.g., HbA1c) then this relationship can be a useful metric in monitoring progression of a disease of efficacy of therapy.

At step 1014, alerts/messages are generated in response to the calculated AGE concentration level. For example, in embodiments in which the ratio calculation and calculation of the AGE concentration level is done locally on the medical device 100 and/or 110, an audio and/or visual alert may be provided to the patient directly indicating the calculated AGE concentration level. In addition, the calculated AGE concentration level may be communicated to a remote monitoring center for provision to the patient's physician. In other embodiments, the ratio calculation and calculation of AGE concentration levels are done remotely. In response to the ratio exceeding a defined threshold, an alert may communicated to the patient's physician or may be communicated to the patient via a messaging system.

In this way, FIGS. 5-11 illustrate various ways in which AGE concentration levels in patient tissue and/or blood may be monitored. In one embodiment (shown in FIGS. 5-7), a single excitation source is utilized in combination with at least two detectors. The emission wavelengths monitored by the at least two detectors correspond with a maximum of the emission response of the targeted AGE molecule and a significant minimum. In another embodiments (shown in FIGS. 8 and 9), a pair of excitation sources are utilized in combination with at least one detector. The first and second excitation sources emit light at first and second excitation wavelengths selected to generate an emission response targeting the AGE molecule to be monitored. This may include selecting an excitation wavelength that corresponds with a maximum emission response (e.g., maximum absorption, autofluorescence, etc.) of the AGE molecule to be monitored in combination with a minimum emission response (e.g., minimum absorption, autofluorescence, etc.) of the same AGE molecule. In other embodiments, the first excitation wavelength may be selected to correspond with a maximum emission response of a first AGE molecule and the second excitation wavelength may be selected to correspond with a maximum emission response of a second molecule (e.g., Hb). In another embodiment (shown in FIGS. 10 and 11), utilizing either combination of excitation sources and photodetectors described above, autofluorescence decay is monitored in lieu of amplitude/intensity of the emission response. The autofluorescence decay may be measured in terms of time required for the emission response to delay from a peak value to a threshold decay value, rate of change (slope) or may be quantified as an average value and/or integral of the fluorescence decay. Depending on the combination of excitation sources and emission detectors, at least a first autofluorescence decay is measured and a second autofluorescence decay is measured, wherein the ratio is utilized to determine concentration of an AGE molecule.

Figure 12:
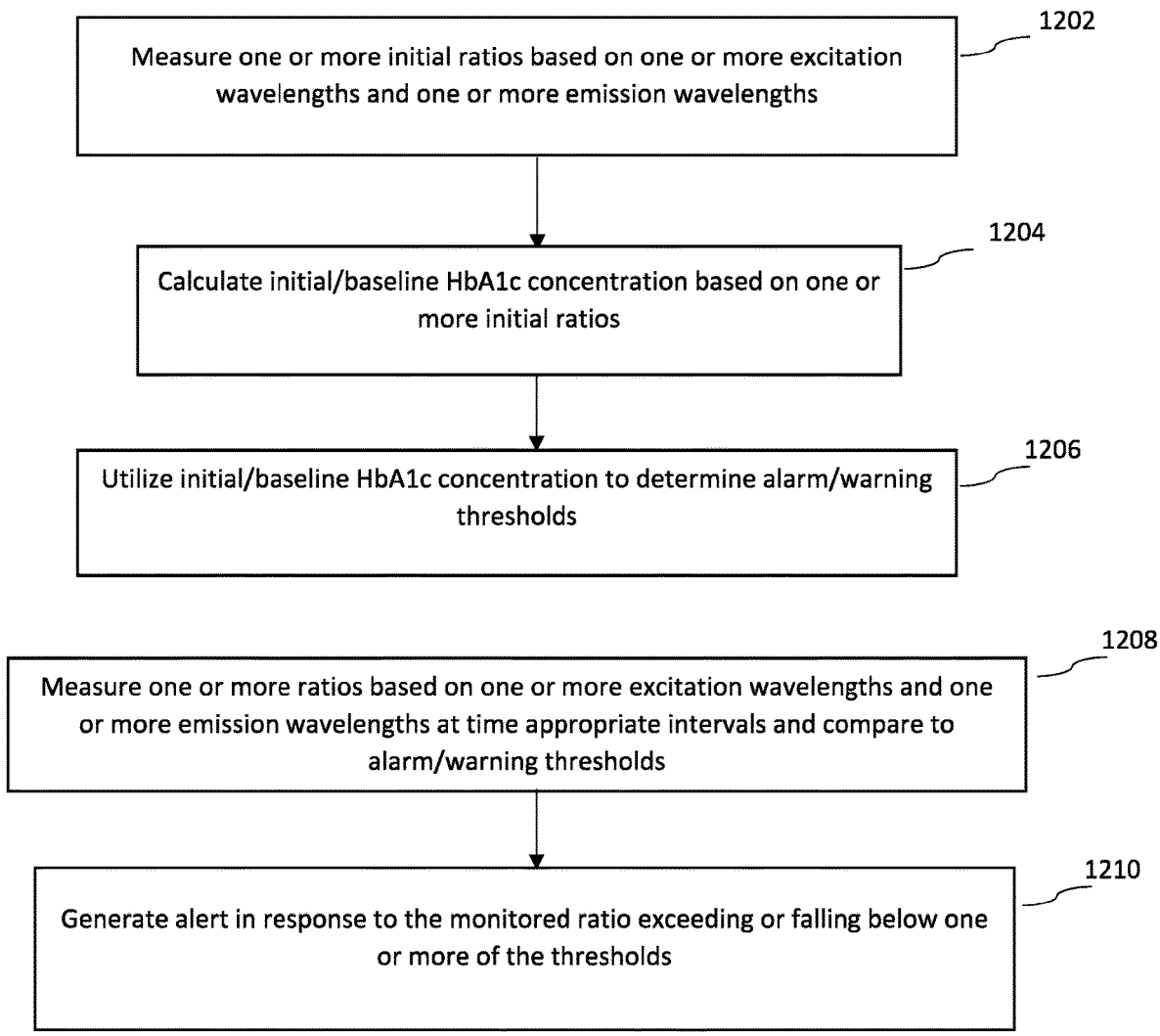
FIG. 12 is a flowchart that illustrates a method of long-term monitoring of HbA1c concentrations according to an embodiment of the present invention.

FIG. 12 is a flowchart that illustrates long-term (e.g., chronic) monitoring and storage of a particular species of AGE, (e.g. glycosylated hemoglobin A1c (HbA1c)).

At step 1202, one or more initial ratio(s) are measured based on one or more excitation wavelengths and one or more emission wavelengths. For example, as discussed with respect to FIG. 5, an excitation wavelengths are utilized to generate an emission response that is monitored with respect to a first emission wavelength and a second emission wavelength. In this embodiment, a light source is utilized along with at least two photodetectors, but in other embodiments a two or more light sources may be utilized in conjunction with a single photodetector.

At step 1204, the HbA1c concentration is calculated based on the initial ratio(s) and is stored as a personalized/baseline HbA1c value associated with the patient. Determining a personalized/baseline HbA1c value may be useful in long-term monitoring of the patient. For example, long-term monitoring of HbA1c values from a baseline value may be useful in assessing patient compliance with diabetes medication, monitoring the progression of diseases such as diabetes, and/or monitoring the stability of the disease.

At step 1206, the personalized/baseline HbA1c value is utilized to set alarm/warning thresholds. Alarm/warning thresholds may be set based on both the personalized/baseline HbA1c value as well as based on fixed HbA1c levels. For example, in some embodiments the monitored HbA1c values are compared to fixed threshold values to determine whether the patient's glycosylated hemoglobin levels have exceeded or fallen below the threshold value. In other embodiments, for example with respect to monitoring disease stability and/or progression, the monitored HbA1c values are compared to the initial or personalized HbA1c value. In some embodiments, the alarm/warning thresholds are set to notify the patient and/or medical personnel in response to progression of diseases such as diabetes based on the monitored HbA1c values. As the disease progresses, the HbA1c concentration level increases. In this way, the alarm/warning thresholds can be utilized to monitor patient compliance with diabetes medication, disease stability, and/or disease progression.

At step 1208, one or more ratios are monitored, utilized to calculate an HbA1c concentration level, and compared to the alarm/warning thresholds to detect patient conditions. For example, if the measured HbA1c concentration level increases, this is an indication that the patient is not taking the prescribed medication, or that the disease is progressing and requires additional therapeutic interventions.

At step 1210, an alert is generated in response to the monitored ratio exceeding or falling below one or more of the thresholds. In some embodiments, when a threshold is crossed, this triggers additional measurements in order to confirm the accuracy of the result. This may include increasing the frequency at which readings are taken, or simply continuing to monitor to ensure that the measured ratios are accurate.

The alert may be provided to the patient in the form of an audio or visual alert. The alert may also be communicated to the intermediate gateway 102 or remote monitoring center 106 (shown in FIG. 1). The alert may be provided to a physician or expert for analysis and confirmation of the detected patient condition.

One of the benefits of the embodiment described with respect to FIG. 12, in combination with adherent and/or insertable devices is that they allow for long-term monitoring of trends in HbA1c concentration levels. In particular, the utilization of ratios minimizes the effect of external influences and noise (such as changing ambient light conditions, etc.), and initialization of the ratio to an average value monitored over an initial monitoring period allows the ratios to be personalized for each patient (to account for differences in the physiology of each patient).

Although the embodiment described with respect to FIG. 12 was specific to HbA1c monitoring as it relates to diabetes detection and pre-diabetes detection, in other embodiments various other AGE molecules may be monitored, both in the patient's bloodstream and/or in patient tissue. For example, evidence of AGE concentration levels in various tissue such as cardiac tissue, dermal tissue, or others may be monitored to detect risk conditions and/or monitor chronic conditions.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A system comprising:
   a medical device comprising:
      a light emitter configured to provide incident light to tissue of a patient at one excitation wavelength; at least one photodetector configured to monitor an emission response to the incident light at a first emission wavelength and at a second emission wavelength; and
      one or more processors configured to:
         determine a concentration of an advanced glycation end-product (AGE) based on a ratio of the emission response at the first emission wavelength to the emission response at the second emission wavelength, wherein the emission response at the first emission wavelength is associated with a maximum of the emission response and the emission response at the second emission wavelength is associated with a minimum of the emission response;

compare the determined concentration to a threshold; and generate an alert based on the comparison.

2. The system of claim 1, wherein the AGE is glycated hemoglobin (HbA1c).

3. The system of claim 2, wherein the one or more processors are configured to determine a risk of diabetes based on the determined concentration of HbA1c.

4. The system of claim 1, wherein the at least one photodetector is configured to monitor an autofluorescence decay of the emission response at the first emission wavelength and the emission response at the second emission wavelength.

5. The system of claim 4, wherein the at least one photodetector is configured to measure a first rate of decay of the emission response at the first emission wavelength and a second rate of decay of the emission response at the second emission wavelength, and the one or more processors are configured to determine the concentration of the AGE based on a ratio of the first rate of decay to the second rate of decay.

6. The system of claim 1, wherein the at least one photodetector is configured to monitor a first amplitude at the first emission wavelength and a second amplitude at the second emission wavelength.

7. The system of claim 1, wherein the one or more processors comprises a processor of the medical device.

8. The system of claim 1, wherein the medical device is configured for implantation in the patient.

9. A method performed by a medical device comprising processing circuitry and being configured to determine a concentration of an advanced glycation end-product (AGE), the method comprising:

providing incident light, by a light emitter of the medical device, to tissue of a patient at one excitation wavelength;

monitoring, by at least one photodetector of the medical device, an emission response to the incident light at a first emission wavelength and at a second emission wavelength;

determining, by the processing circuitry, a concentration of the AGE based on a ratio of the emission response at the first emission wavelength to the emission response at the second emission wavelength, wherein the emission response at the first emission wavelength is associated with a maximum of the emission response and the emission response at the second emission wavelength is associated with a minimum of the emission response;

comparing, by the processing circuitry, the determined concentration to a threshold; and generating, by the processing circuitry, an alert based on the comparison.

10. The method of claim 9, wherein the AGE is glycated hemoglobin (HbA1c).

11. The method of claim 10, further comprising determining, by the processing circuitry, a risk of diabetes based on the determined concentration of HbA1c.

12. The method of claim 9, wherein monitoring the emission response comprises monitoring an autofluorescence decay of the emission response at the first emission wavelength and the emission response at the second emission wavelength.

13. The method of claim 12, wherein monitoring the autofluorescence decay comprises measuring a first rate of decay of the emission response at the first emission wavelength and a second rate of decay of the emission response at the second emission wavelength, and wherein determining the concentration of the AGE comprises calculating the concentration of the AGE based on a ratio of the first rate of decay to the second rate of decay.

14. The method of claim 9, wherein monitoring the emission response comprises monitoring a first amplitude at the first emission wavelength and a second amplitude at the second emission wavelength.

15. The method of claim 9, wherein providing the incident light and monitoring the emission response comprises providing the incident light and monitoring the emission response with the medical device implanted in the patient.

16. The method of claim 9, wherein providing the incident light and monitoring the emission response comprises providing the incident light and monitoring the emission response with the medical device subcutaneously inserted in the patient.

17. A system comprising:

a medical device comprising:
a light emitter configured to provide incident light to tissue of a patient at one excitation wavelength; at least one photodetector configured to monitor a first rate of autofluorescence decay of an emission response to the incident light at a first emission wavelength and a second rate of autofluorescence decay of the emission response at a second emission wavelength; and one or more processors configured to:
determine a concentration of an advanced glycation end-product (AGE) based on a ratio of the first rate of autofluorescence decay of the emission response at the first emission wavelength to the second rate of autofluorescence decay of the emission response at the second emission wavelength.

18. The system of claim 17, wherein the AGE is glycated hemoglobin (HbA1c).

* * * * *